United States Patent
Murphy et al.

(10) Patent No.: US 7,365,232 B2
(45) Date of Patent: Apr. 29, 2008

(54) PROCESS FOR PREPARING A POLYFORMYL ARYLAMINE

(75) Inventors: Leanne D. Murphy, Toronto (CA); Roger E. Gaynor, Oakville (CA)

(73) Assignee: Xerox Corporation, Norwalk, CT (US)

( * ) Notice: Subject to any disclaimer, the term of this patent is extended or adjusted under 35 U.S.C. 154(b) by 274 days.

(21) Appl. No.: 11/116,255

(22) Filed: Apr. 28, 2005

(65) Prior Publication Data
US 2006/0246365 A1    Nov. 2, 2006

(51) Int. Cl.
*C07C 209/68* (2006.01)
*C07C 209/78* (2006.01)

(52) U.S. Cl. .................................... 564/433
(58) Field of Classification Search ............. None
See application file for complete search history.

(56) References Cited

U.S. PATENT DOCUMENTS

| | | |
|---|---|---|
| 3,121,006 A | 2/1964 | Middleton et al. |
| 4,298,697 A | 11/1981 | Baczek et al. |
| 4,338,390 A | 7/1982 | Lu |
| 4,560,635 A | 12/1985 | Hoffend et al. |
| 6,172,264 B1 | 1/2001 | Kobayashi et al. |

OTHER PUBLICATIONS

Database CAPLUS on STN, Acc. No. 1989:144959, Yamada et a.l, JP 63206758 (Aug. 26, 1988) (abstract).*
Database CAPLUS on STN, Acc. No. 2001:133030, Zhou et al., Ranliao Gongye (2000),37(5), p. 31-32,9 (abstract).*
Miyake et al., Organic Process Research and Development (2002), 6, p. 922-925.*
Downie, Ian M., et al., "Vilsmeier Formylation and Glyoxylation Reactions of Nucleophilic Aromatic Compounds Using Pyrophosphoryl Chloride," *Tetrahedron*, 49(19):4015-4034 (1993).
Dyer, Ulrich, C., et al., "Scale-Up of a Vilsmeier Formylation Reaction: Use of HEL Auto-MATE and Simulation Techniques for Rapid and Safe Transfer to Pilot Plant from Laboratory," *Organic Process Research & Development*, 6:311-316 (2002).
Sayah, Babak et al., "Highly Regioselective Vilsmeier-Haack Acylation of Hexahydropyrroloindolizine," *J. Org. Chem.*, 66:2522-2525 (2001).

* cited by examiner

*Primary Examiner*—Brian J. Davis
(74) *Attorney, Agent, or Firm*—MH2 Technology Law Group LLP

(57) ABSTRACT

A process including reacting a substituted or unsubstituted arylamine or a mixture thereof with a Vilsmeier reagent in the presence of a weakly polar liquid.

14 Claims, No Drawings

PROCESS FOR PREPARING A POLYFORMYL ARYLAMINE

FIELD OF THE INVENTION

This disclosure relates to a process comprising reacting a substituted or unsubstituted arylamine or a mixture thereof with a Vilsmeier reagent in the presence of a weakly polar liquid.

BACKGROUND OF THE DISCLOSURE

In a Vilsmeier-Haack reaction, aldehyde or formyl groups can be introduced onto an aromatic ring to yield a formylated-aryl moiety. The reaction entails the formation of a Vilsmeier reagent which then reacts with an aromatic ring of an activated molecule such as a phenol or aromatic amine. The reaction is typically described as a neat process i.e., no solvent is used. Monoformylation occurs rapidly, while the bisformylation reaction has much lower reactivity and occurs more slowly. For example, high purity bisformylation of a triarylamine through a Vilsmeier reaction has been shown to require long reaction periods, such as 96 hours, and excess amounts of the Vilsmeier reagent to obtain adequate conversion. The resulting reaction mixture can be extremely viscous resulting in safety and manufacturing issues.

Solvent-based procedures have been used in manufacturing in order to control the heat of reaction and to provide sufficient agitation to the reaction mixture. Commonly used solvents include toluene, xylene, chlorobenzene, dichlorobenzene, and dichloromethane. Use of these solvents in the reaction mixture generally results in a mixture of mono- and bisformylated products. Complete conversion to the bisformylated product appears to be inhibited by the presence of most solvents, thus requiring vigorous purification techniques in order to isolate a pure bisformylated product.

Methods of forcing the Vilsmeier-Haack reaction to completion i.e., complete bisformylation, include a long reaction time, such as 96 hours; an elevated temperature, and excess Vilsmeier reagent. An elevated temperature, such as from about 90° C. to about 110° C. above the decomposition of the Vilsmeier reagent can result in an intractable black tar that is neither organic nor aqueous soluble possibly due to the decomposition of the reactants. The tar can pose difficulties in using and cleaning the devices and equipment used in the reaction process. An excess of Vilsmeier reagent can be about 5 times the equivalent number of formyl groups being introduced into the organic substrate.

Moreover, the addition of solvents to reduce the viscosity of the mixture appears to inhibit the complete conversion of the triarylamine. U.S. Pat. No. 6,172,264 discloses a process for preparing a poly-formyl-substituted triphenylamine derivative comprising allowing a triphenyamine derivative to react with a Vilsmeier reagent in the presence of toluene and an acid selected from the group consisting of Lewis acids and protonic acids, and then subjecting the reaction product to hydrolysis with an alkaline aqueous solution.

SUMMARY OF THE DISCLOSURE

In various aspects of the disclosure, there is provided a process comprising reacting a substituted or unsubstituted arylamine or a mixture thereof with a Vilsmeier reagent in the presence of a weakly polar liquid; a polyformyl arylamine compound prepared by reacting a substituted or unsubstituted arylamine or a mixture thereof with a Vilsmeier reagent in the presence of a weakly polar liquid; and a photoconductive imaging member comprising a charge transport layer comprising a a charge transport material selected from the group consisting of a hydrazone formed from a polyformyl arylamine, a polyformyl arylamine, and mixtures thereof, wherein the polyformyl arylamine is prepared by reacting a substituted or unsubstituted arylamine or a mixture thereof with a Vilsmeier reagent in the presence of a weakly polar liquid.

Additional objects and advantages of the disclosure will be set forth in part in the description which follows, and in part will be obvious from the description, or can be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DESCRIPTION OF THE EMBODIMENTS

The present disclosure relates to a process for preparing a polyformyl arylamine comprising reacting a substituted or unsubstituted arylamine or a mixture thereof with a Vilsmeier reagent in the presence of a weakly polar liquid. The Vilsmeier reagent can be prepared from an N-substituted formamide and a halogeriating agent. In various embodiments, the electrophilicity of the reactants can be increased by using pyrophosphoryl chloride as the halogenating agent. In various embodiments, the electrophilicity of the reactants can be increased by using an acid selected from the group consisting of a Lewis acid and a protonic acid. In various embodiments, the electrophilicity of the reactants can be increased by using an ionic liquid.

By increasing the electrophilicity of the reactants, and thereby increasing their stability at higher temperatures, it is believed, without being limited to any particular theory, that the reaction can proceed to completion in a shorter period of time. The term "completion" and its grammatical equivalents as used herein is understood to mean that at least 90%, for example at least 92%, and as a further example at least 97% of the substituted or unsubstituted arylamine or a mixture thereof is converted to a polyformyl arylamine.

In an embodiment, the Vilsmeier reagent can be used in a Vilsmeier-Haack reaction. A "Vilsmeier-Haack reaction" is understood to mean the formulation of activated aromatic or heterocyclic compounds with a N-substituted formamide and a halogenating agent.

Non-limiting examples of a N-substituted formamide for use as a formylating agent include N,N-dimethylformamide, N-methylformanilide, N-formylmorpholine, and N,N-diisopropylformamide. In an embodiment, the N-substituted formamide can be N,N-dimethylformamide and N-methylformanilide.

Non-limiting examples of the halogenating agent which can react with the N-substituted formamide to produce a Vilsmeier reagent include phosphorus oxychloride, pyrophosphoryl chloride, phosgene, oxalyl chloride, thionyl chloride, triphenylphosphine-bromine complex, and hexachlorotriphosphor triene. In an embodiment, the halogenating reagent can be selected from phosphorus oxychloride, pyrophosphoryl chloride, phosgene, and thionyl chloride. In an embodiment, the electrophilicity of the Vilsmeier Reagent can be increased by using, for example, pyrophosphoryl chloride, which is known to increase the stability of the reagent at higher temperatures.

The reaction can be carried out by a process which can comprise adding to a reaction vessel from about 2 to about 8, for example from about 3 to about 7, and as a further example from about 3 to about 5, molar equivalents of a N-substituted formamide. In addition, from about 1 to about 8, for example from about 1 to about 6, and as a further example from about 1 to about 4 molar equivalents of a halogenating reagent can be added dropwise to the reaction vessel to prepare a Vilsmeier reagent in situ. Moreover, about 1 equivalent of a substituted or unsubstituted arylamine can be added to the reaction vessel. It is believed, without being limited to any particular theory, that lesser amounts of the Vilsmeier reagent can be needed for completion in the disclosed process, for example 3 molar equivalents, and as a further example 4 molar equivalents of a Vilsmeier reagent to a substituted or unsubstituted arylamine or a mixture thereof.

In another embodiment, the electrophilicity of the reactants can be increased by using an acid selected from the group consisting of a Lewis acid and a protonic acid. These acids can be used to stabilize the system when a Vilsmeier reagent of lower electrophilicity is used, thereby allowing higher temperature without decomposition of the substituted or unsubstituted arylamine or a mixture thereof. This process can also be applied to a commercially available solid Vilsmeier reagent, N,N-dimethylchloromethyleneiminium chloride ($C_3H_7Cl_2N$). This molecule does not cause bisformylation of arylamines under normal reaction conditions due to its lower electrophilicity and its inability to form a homogenous reaction mixture without the presence of a solvent. The weakly polar liquid can allow the solid to melt at a high temperature and therefore react with the substituted or unsubstituted arylamine or a mixture thereof. Non-limiting examples of the Lewis acid include zinc chloride, zinc bromide, boron trifluoride, copper chloride, aluminum chloride, titanium tetrachloride, tin chloride, and the like. Non-limiting examples of the protonic acid include hydrogen chloride, hydrogen bromide, and the like. The acid can be present in any desired or effective amount, such as at least 1 equivalent, and for example 2 molar equivalents. The term "at least 1" is understood to mean one or more molar equivalents, such as 2, 3, 4, or etc. molar equivalents.

In another embodiment, the electrophilicity of the Vilsmeier reagent can be improved by the use of an ionic liquid, such as those possessing a Lewis acid or protonic acid group, which can lend electrophilicity to the reagent without compromising it. For example, the ionic liquid can be synthesized from components such as zinc chloride and (2-bromoethyl)tri-methyl ammonium bromide.

The substituted or unsubstituted arylamine or a mixture thereof for use in the disclosed process can be represented by the following formula (I):

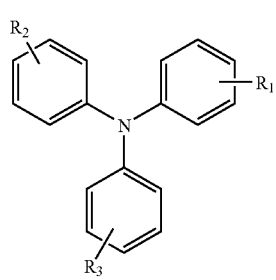

(I)

wherein $R_1$, $R_2$, and $R_3$, can independently be the same or different, and can represent a hydrogen atom, a lower alkyl group, an alkoxy group, a phenoxy group, a halogen atom such as fluoride, chloride, or bromide, or an aryl group or substituted aryl group. The lower alkyl group can have from about 1 to about 15 carbon atoms, for example from about 2 to about 10 carbon atoms. In an embodiment, the lower alkyl group can be selected from the group consisting of methyl, ethyl, propyl, butyl, pentyl, and hexyl groups. The aryl or substituted aryl group can comprise from about 6 to about 30 carbon atoms, and for example from about 6 to about 20 carbon atoms, such as phenyl, naphthyl, phenaphthyl, biphenyl, and the like. Illustrative examples of substituted aryl are methylphenyl, ethylphenyl, propylphenyl, butylphenyl, dimethylphenyl, trimethylphenyl, tetramethylphenyl and the like.

The substituted or unsubstituted arylamine or a mixture thereof can have limited solubility in liquids at ambient temperature. For example, the substituted or unsubstituted arylamine can solubilize appreciably at temperatures greater than 50° C., for example greater than 90° C., and as a further example greater than 110° C.

In an embodiment, completion of the Vilsmeier-Haack reaction can be achieved without long reaction times, e.g., 96 hours, by increasing the electrophilicity of the reactants, thereby increasing their stability at higher temperatures. In an embodiment, the higher reaction temperature is not limited by the use of a weakly polar liquid. Moreover, as discussed above, the use of a weakly polar liquid can alleviate the necessity of excess Vilsmeier reagent for stirring and dissolution.

It is believed, without being limited to any particular theory, that a decrease in the polarity of the liquid, such as a solvent, as measured on a polarity index (0-7), linearly increases the rate of reaction. For example, the medium with the lowest polarity can be found to have a similar rate of reaction to a neat system. In an embodiment, a weakly polar liquid can have a polarity less than about 2, and for example from about 0 to about 1.5. In embodiments, the weakly polar liquid can be nonpolar, for example, can have a polarity of 0 to about 0.5. In an embodiment, a "nonpolar liquid" is understood to mean a substance whose molecules possess no permanent electric moments. Moreover, the molecule does not ionize, or ionizes weakly, in solution.

The reaction vessel can also comprise any desired or effective amount of a weakly polar liquid. The amount of the weakly polar liquid used in the disclosed process can vary and can be readily determined by one of ordinary skill in the art. For example, the weakly polar liquid can be present in the process in a temperature controlling amount, such as at least 1 molar equivalent, for example 2 molar equivalents.

One of ordinary skill in the art would know how to select a weakly polar liquid that has a boiling point above the reaction temperature. For example, if the reaction temperature was chosen to be about 80° C., one of ordinary skill in the art can select a cyclohexane for use in the disclosed process. As a further example, if the reaction temperature was chosen to be about 120° C., one of ordinary skill in the art can select an ISOPAR® (available from Exxon Mobil Corporation) with a high boiling point, for example 129° C., for use in the disclosed process.

Non-limiting examples of a weakly polar liquid which can be used in the disclosed process include the ISOPAR® series (manufactured by the Exxon Corporation). These hydrocarbon liquids can be considered narrow portions of isoparaffinic hydrocarbon fractions with extremely high levels of purity. For example, the boiling range of ISOPAR C® can be from about 96° C. to about 107° C.; ISOPAR E® can be from about 113° C. to about 143° C.; ISOPAR G® can be from about 157° C. to about 176° C.; ISOPAR H® can be from about 176° C. to about 191° C.; ISOPAR K® can be from about 177° C. to about 197° C.; ISOPAR L® can be from about 188° C. to about 206° C.; ISOPAR M® can be from about 207° C. to about 254° C.; and ISOPAR V® can be from about 254.4° C. to about 329.4° C. ISOPAR L® has a mid-boiling point of approximately 194° C. ISOPAR M® has an auto ignition temperature of about 338° C. ISOPAR G® has a flash point of 40° C. as determined by the tag closed cup method. ISOPAR H® has a flash point of 53° C. as determined by the ASTM D-56 method. ISOPAR L® has a flash point of 61° C. as determined by the ASTM D-56 method; and ISOPAR M® has a flash point of 80° C. as determined by the ASTM D-56 method.

The reaction can be effected at temperatures from about room temperature (23° C.) to about 150° C., for example from about 85° C. to about 120° C., and as a further example from about 98° C. to about 120° C. The increase in temperature can make the completion of the conversion of the substituted or unsubstituted arylamine or a mixture thereof to the polyformyl arylamine proceed faster, for example less than about 96 hours, as a further example less than about 10 hours, and as another example from about 6 to about 10 hours.

In order to synthesize a polyformyl arylamine, the reaction can be effected in the above disclosed temperature ranges to obtain a diiminium salt of arylamine. The iminium salt thus obtained can then be subjected to hydrolysis with an aqueous solution, wherein the solution can be alkaline, neutral, or acidic. For example, the aqueous solution can be selected from the group consisting of water or an alkali such as sodium hydrogencarbonate, sodium carbonate, potassium carbonate, sodium hydroxide, potassium hydroxide, and sodium acetate.

The polyformyl arylamine prepared by the process disclosed herein can be represented by the following formula (II):

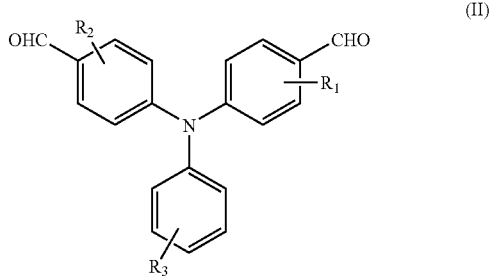

wherein $R_1$, $R_2$, and $R_3$ can be as defined above with respect to formula (I).

The polyformyl arylamine can be used to form a hydrazone. One of ordinary skill in the art would know how to form a hydrazone from a polyformyl arylamine. The hydrazone can be used as a charge-transport material. The charge-transport material can be used in a photoconductive imaging member.

The photoconductive imaging member can comprise a substrate, an optional blocking layer, a photogenerating layer, a charge transport layer, and optionally thereover an overcoat layer that can comprise a polymer with a low dielectric constant and charge transport molecules.

The photogenerating layer can comprise photogenerating pigments dispersed in a resinous binder. The photogenerating pigments can be present in any effective or desired amount, such as from about 5% to about 95% by weight, for example from about 10% to about 80%, and as a further example from about 20% to about 70%. Non-limiting examples of photogenerating layer components include trigonal selenium, titanyl phthalyocyanines, perylenes, hydroxygallium phthalocyanine, metal phthalocyanines, vanadyl phthalocyanines, and metal free phthalocyanines. The resinous binder can be selected from the group consisting of polyesters, polyvinyl butyrals, polycarbonates, polystyrene-b-polyvinyl pyridine, and polyvinyl formals.

The photoconductive imaging members can be selected from a number of different known imaging and printing processes including, for example, color processes, digital imaging process, digital printers, PC printers, and electrophotographic imaging processes, for example xerographic imaging and printing processes wherein charged latent images can be rendered visible with toner compositions of an appropriate charge polarity.

In an embodiment, there is disclosed a method of imaging that can comprise generating an electrostatic latent image on an imaging member, developing the latent image, and transferring the developed electrostatic image to a suitable substrate.

The substrate layer can be opaque or substantially transparent, and can comprise any suitable material having the requisite mechanical properties. Thus, the substrate can comprise a layer of insulating material including inorganic or organic polymeric materials, such as MYLARE® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate can be flexible, seamless, or rigid, and can have a number of many different configurations, such as for example a plate, a cylindrical drum, a scroll, an endless flexible belt, and the like. In one embodiment, the substrate can be in the form of a seamless flexible belt. In some situations, it can be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer can be of substantial thickness, for example in excess of about 3,000 microns, or of a minimum thickness. In embodiments, the thickness of this layer can be from about 75 microns to about 300 microns, and more specifically, from about 70 to about 150 microns.

The photogenerating layer can contain known photogenerating pigments, such as metal phthalocyanines, metal free phthalocyanines, hydroxygallium phthalocyanines, perylenes, such as bis(benzimidazo) perylene, titanyl phthalocyanines, and the like, and more specifically, vanadyl phthalocyanines, Type V hydroxygallium phthalocyanines, Type IV titanyl phthalocyanine, and inorganic components, such as selenium, especially trigonal selenium. The photogenerating pigment can be dispersed in a resin binder, or alternatively no resin binder can be needed. Generally, the thickness of the photogenerator layer depends on a number of factors, including the thicknesses of the other layers and the amount of photogenerator material contained in the photogenerating layers. Accordingly, this layer can be of a thickness of, for example, from about 0.05 micron to about 10 microns, and more specifically, from about 0.25 micron to about 3 microns when, for example, the photogenerator compositions are present in an amount of from about 30 to about 75 percent by volume. The maximum thickness of the layer in an embodiment can be dependent primarily upon factors, such as photosensitivity, electrical properties and mechanical considerations. The photogenerating layer binder resin, present in various suitable amounts, for example from about 1 to about 50, and more specifically, from about 1 to about 10 weight percent, can be selected from a number of known polymers, such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. In embodiments of the present disclosure, it can be desirable to select a coating solvent that does not substantially disturb or adversely affect the other previously coated layers of the device. Non-limiting examples of solvents that can be selected for use as coating solvents for the photogenerator layer include ketones, alcohols, aromatic hydrocarbons, halogenated aliphatic hydrocarbons, ethers, amines, amides, esters, and the like. Specific non-limiting examples include cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like.

The coating of the photogenerator layers in embodiments of the present disclosure can be accomplished with spray, dip or wire-bar methods such that the final dry thickness of the photogenerator layer can be, for example, from about 0.01 to about 30 microns, and more specifically, from about 0.1 to about 3 microns after being dried at, for example, about 40° C. to about 150° C. for about 15 to about 90 minutes.

Illustrative examples of polymeric binder materials that can be selected for the photogenerator layer can be as indicated herein, and include those polymers as disclosed in U.S. Pat. No. 3,121,006, the disclosure of which is totally incorporated herein by reference. In general, the effective amount of polymer binder that can be utilized in the photogenerator layer can be from about 0 to about 95 percent by weight, and for example from about 25 to about 60 percent by weight of the photogenerator layer.

As optional adhesives usually in contact with the supporting substrate layer, there can be selected various known substances inclusive of polyesters, polyamides, poly(vinyl butyral), poly(vinyl alcohol), polyurethane and polyacrylonitrile. This layer can be, for example, of a thickness of from about 0.001 micron to about 1 micron. Optionally, this layer can contain effective suitable amounts, for example from about 1 to about 10 weight percent, of conductive and nonconductive particles, such as zinc oxide, titanium dioxide, silicon nitride, carbon black, and the like, to provide, for example, in embodiments of the present disclosure, desirable electrical and optical properties.

Generally, the charge transport layer contains from about 10 to about 75 percent by weight of the charge transport material, and more specifically, from about 35 percent to about 50 percent of this material. The charge transport material can be selected from the group consisting of a hydrazone formed from the disclosed polyformyl arylamine, the disclosed polyformyl arylamine, and mixtures thereof. In an embodiment, the charge transport material can be present in the charge transporting layer, which generally can be of a thickness of from about 5 microns to about 80 microns, and for example can be of a thickness of from about 10 microns to about 44 microns.

Non-limiting examples of the overcoat layer, which layer in embodiments can be of a thickness, for example, of about 0.1 to about 25, more specifically from about 1 to about 10, and yet more specifically from about 1 to about 5 microns, in contact with the charge transport layer or in embodiments the photogenerating layer, include a low dielectric constant (E<2.5) polymer and a charge transport molecule, or charge transport molecule mixtures with a weight ratio of, for example, from about 30/70 to about 80/20, more specifically from about 50/50 to about 75/25, and yet more specifically from about 60/40 to about 75/25. Polymer examples are amorphous poly(phenylene ethers), available from Creanova Inc. as VESTORAN 1900 PPE™ with a glass transition temperature, $T_g$, of 190° C. and a dielectric constant of 2; poly(cyclo olefins) PCOs available from Zeon Chemical as ZEONOR 1600™, with a $T_g$ of 163° C. and a dielectric constant of 2.27; heat resistant poly(cyclohexylenedimethylene terephthalates) PCTs available from Eastman Chemical as EASTAR AN004™ copolyesters with a temperature of deflection greater than 103° C. and a dielectric constant of 2.1; nylon 12 available from Creanova Inc. as VESTAMIDE L1940™ with a temperature of deflection equal to 110° C. and a dielectric constant equal to 2; fluorinated polymers available from E. I. DuPont Company as 4100 FEP™, a fluorinated ethylene propylene polymer with a melting temperature equal to 259° C. and a dielectric constant equal to 2; polystyrene available from Creanova Inc. as VESTYRON 325™ with a glass transition temperature equal to 89° C. and a dielectric constant equal to 2, and polypropylene available from BASF as NOVOLEN™ with a Viscat softening temperature equal to 92° C. and a dielectric constant equal to 2.3.

Also included within the scope of the present disclosure are methods of imaging and printing with the photoresponsive devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device can be used in a printing mode, the imaging method involves the same steps with the exception that the exposure step can be accomplished with a laser device or image bar.

EXAMPLES

Example 1

Vilsmeier-Haack Reaction in the Presence of Zinc Chloride and ISOPAR L®

Into a 500 ml reaction flask the following were charged: 25.71 g (0.08 mol) of a substituted or unsubstituted arylamine or a mixture thereof, 10.9 g (0.08 mol) of zinc chloride, 17.54 g (0.24 mol) of N,N-dimethylformamide and 30 g ISOPAR L®. 36.79 G (0.24 mol) of phosphorus oxychloride was added dropwise to the reaction mixture under nitrogen. The reaction mixture was heated to 120° C.

under nitrogen and stirring. The temperature was maintained for 7 hours with sample drawn intermittently. Samples were analyzed by high performance liquid chromatography (HPLC) to determine reaction conversion. The HPLC results are set forth in Table 1.

Comparative Example 1

Vilsmeier-Haack Reaction in the Presence of Zinc Chloride and Toluene

Into a 500 ml reaction flask 14.62 g (0.2 mol) of N,N-dimethylformamide was charged. 30.67 g (0.2 mol) of phosphorous oxychloride was added dropwise to the reaction mixture under nitrogen and cooling. 12.86 g (0.04 mol) of the substituted or unsubstituted arylamine or a mixture thereof used in Example 1, 5.45 g (0.04 mol) of zinc chloride and 174.45 g of toluene were then charged to the reactor. The reaction mixture was heated to 90° C. under nitrogen and stirring. The temperature was maintained for 29 hours with samples drawn intermittently. Samples were analyzed by HPLC to determine reaction conversion. The HPLC results are set forth in Table 1.

Comparative Example 2

Vilsmeier-Haack Reaction in the Absence of Zinc Chloride and Liquid

Into a 500 ml reaction flask the following were charged: 70.55 g (0.22 mol) of the substituted or unsubstituted arylamine or a mixture thereof of Example 1 and 80.2 g (1.1 mol) of N,N-dimethylformamide. 168.3 g (1.1 mol) of phosphorous oxychloride was added dropwise to the reaction mixture under nitrogen and cooling. The reaction mixture was heated to 90° C. under nitrogen and stirring. The temperature was maintained for 96 hours with samples drawn intermittently. Samples were analyzed by HPLC to determine reaction conversion. The HPLC results are set forth in Table 1.

TABLE 1

| | Time (h) | % Bisformyl Arylamine | % Monoformyl Arylamine |
| --- | --- | --- | --- |
| Example | 7 | 97.4 | 1.4 |
| Comparative Ex. 1 | 29 | 85.7 | 10.7 |
| Comparative Ex. 2 | 96 | 97.91 | 0 |

The breakthrough was demonstrated in a reduction of the reaction time from 96 hours to 6-10 hours, which can offer an advantage in the manufacturing cost of a polyformyl arylamine. The improved reaction conditions, including the use of reduced amounts of Vilsmeier reagent, such as down to 3:1 molar equivalents, have resulted in cleaner reactions comprising purer products and increased throughputs.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a weakly polar liquid" includes two or more different weakly polar liquids. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A process comprising reacting a substituted or unsubstituted arylamine or a mixture thereof with a Vilsmeier reagent in the presence of a weakly polar liquid to form a polyformyl arylamine.

2. The process of claim 1, wherein the weakly polar liquid does not affect the reaction rate.

3. The process of claim 1, wherein the process is conducted at a reaction temperature from about room temperature to about 150° C.

4. The process of claim 1, wherein the reaction temperature is from about 98° C. to about 120° C.

5. The process of claim 1, further comprising increasing a reaction temperature and thereby decreasing a reaction time to achieve at least 90% conversion of the substituted or unsubstituted arylamine or mixture thereof to the polyformyl arylamine.

6. The process of claim 5, wherein the reaction time is about 96 hours.

7. The process of claim 5, wherein the reaction time is less than about 10 hours.

8. The process of claim 5, wherein the reaction time is about 6 to about 10 hours.

9. The process of claim 1, wherein the weakly polar liquid is present in a temperature controlling amount.

10. The process of claim 9, wherein the weakly polar liquid is present in at least 1 molar equivalent to the substituted or unsubstituted arylamine or a mixture thereof.

11. The process of claim 1, further comprising increasing the electrophilicity of the Vilsmeier reagent by adding an ionic liquid.

12. The process of claim 1, wherein the weakly polar liquid has a boiling point ranging from about 96° C. to about 329.4° C.

13. The process of claim 1, further comprising increasing the electrophilicity of the Vilsmeier reagent by adding an acid selected from the group consisting of a Lewis acid and a protonic acid.

14. The process of claim 1, wherein the weakly polar liquid has a polarity of less than about 2.

* * * * *